US012558203B2

(12) United States Patent
Jahns et al.

(10) Patent No.: US 12,558,203 B2
(45) Date of Patent: Feb. 24, 2026

(54) DENTAL MILL BLANK OF A POROUS ZIRCONIA MATERIAL CONTAINING OXIDES OF Tb, Er AND Cr, PROCESS OF PRODUCING AND USE THEREOF

(71) Applicant: Solventum Intellectual Properties Company, Maplewood, MN (US)

(72) Inventors: Michael Jahns, Gilching (DE); Gallus Schechner, Herrsching (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 493 days.

(21) Appl. No.: 17/753,195

(22) PCT Filed: Aug. 27, 2020

(86) PCT No.: PCT/IB2020/058020
§ 371 (c)(1),
(2) Date: Feb. 23, 2022

(87) PCT Pub. No.: WO2021/048674
PCT Pub. Date: Mar. 18, 2021

(65) Prior Publication Data
US 2022/0273404 A1 Sep. 1, 2022

(51) Int. Cl.
| | |
|---|---|
| *A61C 13/00* | (2006.01) |
| *A61C 5/77* | (2017.01) |
| *A61K 6/78* | (2020.01) |
| *A61K 6/818* | (2020.01) |
| *A61K 6/822* | (2020.01) |
| *C04B 35/486* | (2006.01) |
| *C04B 111/00* | (2006.01) |

(52) U.S. Cl.
CPC ............ *A61C 13/0022* (2013.01); *A61C 5/77* (2017.02); *A61K 6/78* (2020.01); *A61K 6/818* (2020.01); *A61K 6/822* (2020.01); *C04B 35/486* (2013.01); *C04B 2111/00836* (2013.01); *C04B 2235/3244* (2013.01); *C04B 2235/6562* (2013.01); *C04B 2235/6567* (2013.01); *C04B 2235/9653* (2013.01)

(58) Field of Classification Search
CPC ........ A61C 13/0022; A61C 5/77; A61K 6/78; A61K 6/818; A61K 6/822; C04B 35/486; C04B 2111/00836; C04B 2235/3244; C04B 2235/6562; C04B 2235/6567; C04B 2235/9653
See application file for complete search history.

(56) References Cited

U.S. PATENT DOCUMENTS

| | | | |
|---|---|---|---|
| 7,985,119 B2 | 7/2011 | Basler | |
| 8,141,217 B2 | 3/2012 | Gubler | |
| 8,541,329 B2 | 9/2013 | Ritzberger | |
| 2007/0292597 A1 | 12/2007 | Ritzberger | |
| 2008/0303181 A1 | 12/2008 | Holand | |
| 2012/0139141 A1 | 6/2012 | Khan | |
| 2012/0214134 A1 | 8/2012 | Khan | |
| 2014/0101869 A1 | 4/2014 | Carden | |
| 2017/0020639 A1 | 1/2017 | Jahns | |
| 2017/0273764 A1 | 9/2017 | Volkl | |
| 2018/0235847 A1 | 8/2018 | Balasubramanian | |
| 2018/0237345 A1 | 8/2018 | Valenti | |
| 2019/0233340 A1 | 8/2019 | Kim | |
| 2020/0170763 A1* | 6/2020 | Jiang | C04B 35/486 |

FOREIGN PATENT DOCUMENTS

| | | | |
|---|---|---|---|
| DE | 20316004 | 3/2004 | |
| DE | 102018103534 | 9/2018 | |
| FR | 2781366 | 10/2000 | |
| WO | WO2013-022612 | 2/2001 | |
| WO | WO2001-013862 | 3/2001 | |
| WO | WO2002-045614 | 6/2002 | |
| WO | WO2012-125885 | 9/2012 | |
| WO | WO2015-084931 | 6/2015 | |
| WO | WO-2015084931 A1* | 6/2015 | A61C 13/00 |
| WO | WO2016-019114 | 2/2016 | |
| WO | WO2017-144644 | 8/2017 | |

OTHER PUBLICATIONS

International Search Report for PCT International Application No. PCT/IB2020/058020, mailed on Sep. 17, 2020, 4 pages.
1507 Extended EP Search Report for EP19196623.3, Date Mar. 18, 2020, 2pages.

* cited by examiner

*Primary Examiner* — Cameron K Miller

(57) ABSTRACT

The present invention relates to a dental zirconia mill blank comprising a porous zirconia material, the porous zirconia material comprising Zr oxide, Y oxide, optionally Al oxide, Bi oxide, Tb oxide, Er oxide, Cr oxide, the porous zirconia material not comprising Fe oxide calculated as $Fe_2O_3$ of more than 0.01 wt. %, Mn oxide calculated as $MnO_2$ of more than 0.005 wt. %, Co oxide calculated as $Co_2O_3$ of more than 0.005 wt. %, wt. % with respect to the weight of the porous zirconia material. The invention also relates to a process of producing such a dental zirconia mill blank and a dental restoration which can be machined from the dental zirconia mill blank. Further, the invention relates to a kit of parts comprising such a dental zirconia mill blank and a dental cement.

11 Claims, No Drawings

DENTAL MILL BLANK OF A POROUS ZIRCONIA MATERIAL CONTAINING OXIDES OF Tb, Er AND Cr, PROCESS OF PRODUCING AND USE THEREOF

CROSS REFERENCE TO RELATED APPLICATIONS

This application is a national stage filing under 35 U.S.C. 371 of PCT/IB2020/058020, filed Aug. 27, 2020, which claims the benefit of European Application No. 19196623.3, filed Sep. 11, 2019, the disclosure of which is incorporated by reference in its/their entirety herein.

FIELD OF THE INVENTION

The invention relates to a dental mill blank comprising a porous zirconia material comprising oxides of Zr, Y, Bi, Tb, Er and Cr.

The invention also relates to a process of producing such a dental mill blank and a dental article from that dental mill blank.

The dental article obtained from the dental mill blank can be sintered with multiple sintering rates without negatively affecting the overall aesthetics of the dental article.

BACKGROUND

Dental mill blanks based on zirconia ceramic materials are described in various documents and are also commercially available.

Dental mill blanks are typically used for producing dental restorations (e.g. crowns and bridges) by a milling process. The zirconia material the dental mill blank is made of, is typically in a pre-sintered and porous stage which facilitates its milling. The obtained dental article is then sintered to its final density before it is placed in the mouth of the patient.

Pure zirconia, however, is white and does not match the natural color of the tooth in the mouth of a patient.

To address this issue, the milled zirconia material is typically treated with certain coloring solutions before sintering.

Most of the coloring solutions, which are also commercially available, contain iron as coloring ion. Iron seems to be a perfect candidate to achieve the desired tooth color.

WO 2012/125885 A1 (3M) relates to a dental ceramic article comprising $ZrO_2$ and $Al_2O_3$ and at least one component comprising Mn, Er or mixtures thereof. It is stated that the ceramic article shows enhanced aesthetic appearance compared with ceramic articles of the state of the art.

WO 2013/022612 A1 (3M) relates to a coloring solution for selectively treating the surface of dental ceramics, the solution comprising a solvent, an effect agent and a complexing agent, the effect caused by the effect agent being either coloring, providing fluorescence or a combination thereof. Elements which were found to be useful include Fe, Mn, Er, Pr, Co and Bi.

US 2008/0303181 A1 (Holand et al.) describes a dental material shaded to match the colors of natural dentition comprising $ZrO_2$ stabilized with cerium oxide, a coloring agent comprising one or more Fe, Pr, Tb, Er, Nd, Eu, Yb and Mn, oxides thereof and combinations thereof.

US 2012/0214134 A1 (Khan et al.) relates to a dental article including yttria stabilized tetragonal zirconia polycrystalline ceramic and no more than 0.15 wt. % of one or more coloring agents of one or more of: Fe, Er, Co, Pr, Tb, Cr, Nd, Ce, V, Eu, Ho, Ni and Cu, oxides thereof and combinations thereof.

FR 2,781,366 A1 (Norton Desmarquest Fine Ceramics) describes an yttrium-stabilized zirconium dioxide ceramic composition for dental prostheses being colored with a pigment blend of iron oxide, bismuth oxide and cerium oxide.

U.S. Pat. No. 8,541,329 B2 (Ivoclar) relates to compositions based on $ZrO_2$ and single- and multi-colored blanks made from oxide ceramics. As a preferred composition based on $ZrO_2$ further contains Pr calculated as $Pr_2O_3$ in an amount of 0.0001 to 0.01 wt. %, Fe calculated as $Fe_2O_3$ in an amount of 0.005 to 0.5 wt. %, Tb calculated as $Tb_2O_3$ in an amount of 0.0001 to 0.1 wt. % and Mn calculated as $Mn_2O_3$ in an amount of 0.0001 to 0.1 wt. %.

US 2018/0237345 A1 (Valenti et al.) describes shaded, zirconia ceramic materials that are suitable for use in dental applications. Ceramic bodies are made from a zirconia-containing ceramic material and a coloring composition comprising a terbium (Tb)-containing component and a chromium (Cr)-containing component as a coloring agent.

US 2018/0235847 A1 (Balasubramanian et al.) describes a zirconia ceramic material for use in dental applications comprising an yttria-stabilized zirconia material comprising from 4.5 mol % to 5.1 mol % yttria. Optionally, the zirconia ceramic has a coloring agent that may comprise one or more metals selected from terbium (Tb), chromium (Cr), erbium (Er), and cobalt (Co), and further, may, optionally, comprise alumina, which if present may be in an amount from 0 wt % to 0.25 wt %.

US 2014/0101869 A1 (Carden et al) describes a coloring liquid for shading pre-sintered ceramic dental restorations, utilizing a combination of metal salt, solvent and acid to achieve natural tooth coloring of standard dental shades. The use of a liquid is suggested comprising in solution: a metallic salt taken from the group consisting of $TbCl_3$, $CrCl_3$ and $MnSO_4$.

US 2007/0292597 A1 (Ritzberger et al.) relates to compositions based on $ZrO_2$, and single- and multi-colored blanks made from oxide ceramics, and a process for their preparation, in which oxide ceramic powder is coated with a coloring substance, the coated powders are preferably graded and at least one colored powder is filled into a compression mould, the colored powder or powders are compressed to produce a shaped body, and the compressed shaped body is sintered to produce a blank. The use of at least one of the elements of Pr, Fe, Tb and Cr is proposed.

US 2012/0139141 A1 (Kahn et al.) describes a dental article, which includes yttria stabilized tetragonal zirconia polycrystalline ceramic, and no more than about 0.15 wt. % of one or more coloring agents of one or more of: Pr, Tb, Cr, Nd, Co, oxides thereof, and combinations thereof, whereby the dental article is provided with a color corresponding to a natural tooth shade; and wherein the dental article has a flexural strength of at least about 800 MPa.

US 2017/0273764 A1 (Volkl et al.) relates to a method for manufacturing a colored blank, which contains zirconium dioxide and is intended for the manufacture of a dental restoration, whereby raw materials in powder form, at least some of which contain one coloring substance each, are mixed with, zirconium dioxide as the main ingredient, the resulting mixture is pressed and subsequently subjected to at least one thermal treatment. To generate the desired fluorescence, it is intended that in the raw materials in powder form one uses as coloring substances at least terbium, erbium, cobalt, as well as one substance that generates a fluorescence effect in the dental restoration, however not iron, aside from naturally occurring impurities.

US 2019/0233340 A1 (Kim et al.) describes a colored ceramic body that has at least one color region and a color gradient region. The colored body is made by unidirectional infiltration of a coloring composition into the ceramic body. Metal-containing components which can be used include the elements of Tb, Cr, Er, Co, Mn, Pr, V, Ti Ni, Cu and Zn.

WO 2015/084931 A1 (3M) describes coloured zirconia ceramic dental mill blank having fluorescing properties. The dental mill blank comprises a porous zirconia material comprising Bi oxide, Tb oxide and optionally one or two of the oxides of Er and Mn, wherein the porous zirconia material is essentially free of either or all of the following oxides: Fe, Cr, Cu, V, Mo and Pr.

WO 2016/019114 A1 (3M) relates to a kit of parts comprising a dental mill blank and a colouring solution for colouring the porous zirconia material. The porous zirconia material comprises Bi oxide as fluorescing agent, but is essentially free of colouring ions like Tb, Pr, Er, Mn and Fe.

However, there is still room for improvement especially with regard to the requirements to be fulfilled with respect to modern dental materials.

DESCRIPTION OF THE INVENTION

Patients and dentists nowadays have an increasing demand for highly aesthetic dental restorations.

In particular, there is desire for a dental material which does not only have the desired tooth color and appearance of a natural dental tooth, there is also a desire for a dental restoration which can be sintered sufficiently fast, thus allowing possibly a so-called chair-side treatment, that is a treatment, where the dental restoration is prepared during the time when the patient is in the dental office.

After such a heat-treatment, the sintered dental restoration should still show the desired aesthetics (e.g. tooth color and/or fluorescent appearance).

Thus, there is a need for a dental material which is sufficiently robust to withstand not only a regular sintering process, but also a fast-sintering process where higher heating rates are applied.

In addition, as there are multiple dental furnaces present in the market, each of which providing different sintering profiles for sintering dental restorations (e.g. sintering cycle from less than 20 min up to about 60 min), there is a need for a dental mill blank from which dental restorations can be machined and sintered without running the risk of obtaining undesired variability in color or translucency depending on the dental furnace used.

At least one of these objectives is addressed by the dental mill blank and related processes described in the present text and claims.

In one embodiment the invention is directed to a dental mill blank as described in the present text and claims comprising a porous zirconia material, the porous zirconia material comprising Zr oxide, Y oxide, optionally Al oxide, Bi oxide, Tb oxide, Er oxide, Cr oxide, the porous zirconia material not comprising Fe oxide calculated as $Fe_2O_3$ of more than 0.01 wt. %, Mn oxide calculated as $MnO_2$ of more than 0.005 wt. %, Co oxide calculated as $Co_2O_3$ of more than 0.005 wt. %, wt. % with respect to the weight of the porous zirconia material.

A further embodiment of the invention is directed to a process of producing a dental mill blank as described in the present text and claims, the process comprising the steps of providing a zirconia powder comprising Tb oxide, providing a zirconia powder comprising Er oxide, providing a zirconia powder comprising Cr oxide, providing a zirconia powder comprising Bi oxide, providing a zirconia powder not comprising oxides of Tb, Er, Cr and Bi, mixing and/or layering the zirconia powders, compacting the layered and/or mixed zirconia powders, optionally applying a heat-treatment step, the zirconia powders comprising Zr oxide, Y oxide and optionally Al oxide, none of the zirconia powders or the dental mill blank comprising oxides of Fe, Mn and Co, Fe oxide in an amount of more than 0.01 wt. %, Mn and Co oxides in an amount of more than 0.005 wt. %.

The invention is also directed to a process of producing a dental restoration and to the dental restoration obtained or obtainable by such a process.

An additional aspect of the invention is directed to the use of a combination of certain elements for the production of a dental restoration by applying a speed-sintering process, i.e. a sintering process using high heating rates of at least 1.5 or 2° C./sec.

Yet still a further aspect of the invention is directed to a kit of parts as described in the present text and claims comprising the dental mill blank and a dental cement.

Unless defined differently, for this description the following terms shall have the given meaning:

The term "dental article" means an article which is to be used in the dental or orthodontic field, especially for producing of or as dental restoration, a tooth model and parts thereof.

A "dental restoration" means a dental article for restoring a defective tooth structure.

A dental restoration typically has a 3-dimensional inner and outer surface. The surface typically includes convex and concave structures. Compared to other articles such as pottery or paving stones, a dental restoration is small and filigree. The thickness of the dental restoration can vary from very thin, e.g. at the edges and rims (below 0.1 mm) to considerably thick, e.g. in the biting area (up to 8 or 16 mm). Sections bridging the crown portions in dental bridges might have a thickness up to 20 mm. The outer surface typically has an overall convex shape, whereas the inner surface typically has an overall concave shape.

The dental restoration described in the present text comprises or essentially consists after sintering of a polycrystalline ceramic material comprising yttrium stabilized zirconia.

Examples of dental articles include crowns (including monolithic crowns), bridges, inlays, onlays, veneers, facings, copings, crown and bridge framework, implants, abutments, orthodontic appliances (e.g. brackets, buccal tubes, cleats and buttons), monolithic dental restorations (i.e. restorations which do not need to be veneered) and parts thereof.

The surface of a tooth is considered not to be a dental article.

A dental article should not contain components which are detrimental to the patient's health and thus free of hazardous and toxic components being able to migrate out of the dental article.

By "dental mill blank" is meant a solid block (3-dim article) of material from which a dental article, dental workpiece, dental support structure or dental restoration can and typically is to be machined in any subtractive process, e.g. besides milling also by grinding, drilling etc.

A dental mill blank has a geometrically defined shape and comprises at least one flat surface. A so-called "free form surface" is not regarded as "geometrically defined". In this respect the shape of a dental restoration (e.g. crown or bridge) itself is not regarded a dental mill blank.

"Zirconia article" shall mean a 3-dimensional article wherein at least one the x,y,z dimensions is at least about 5 mm, the article being comprised of at least 80 or at least 90 or at least 95 wt. % zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monoclinic, cubic zirconia and mixtures thereof.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former and modifier.

The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. It is formed as a glass, and then made to crystallize partly by heat treatment. Glass ceramics may refer to a mixture of lithium-, silicon-, and aluminium-oxides.

The porous dental material described in the present text does not contain a glass-ceramic.

A "powder" means a dry, bulk composed of a large number of fine particles that may flow freely when shaken or tilted.

A "particle" means a substance being a solid having a shape which can be geometrically determined. The shape can be regular or irregular. Particles can typically be analysed with respect to e.g. size and size distribution.

"Density" means the ratio of mass to volume of an object. The unit of density is typically g/cm$^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

An article is classified as "absorbent" if the article is able to absorb a certain amount of a liquid, comparable to a sponge. The amount of liquid which can be absorbed depends e.g. on the chemical nature of the article, the viscosity of the solvent, the porosity and pore volume of the article. E.g. a pre-sintered ceramic article, that is an article which has not been sintered to full density, is able to absorb a certain amount of liquid. Absorbing of liquids is typically only possible if the article has an open-porous structure.

A "porous material" refers to a material comprising a partial volume that is formed by voids, pores, or cells in the technical field of ceramics. Accordingly, an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between 15% and 75% or between 18% and 75%, or between 30% and 70%, or between 34% and 67%, or between 40% to 68%, or between 42% and 67%. The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

"Calcining" refers to a process of heating a solid material to drive off at least 90 percent by weight of volatile chemically bond components (e.g. organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For zirconia based ceramics a typical sintering temperature range is from 1,100° C. to 1,600° C. Sintering typically includes the densification of a porous material to a less porous material (or a material having less cells) having a higher density, in some cases sintering may also include changes of the material phase composition (for example, a partial conversion of an amorphous phase toward a crystalline phase).

A "fluorescing agent" shall mean an agent showing or providing fluorescence in the region of visible light (380 to 780 nm).

By "machining" is meant milling, grinding, cutting, carving, or shaping a material by a machine. Milling is usually faster and more cost effective than grinding. A "machinable article" is an article having a 3-dimensional shape and having sufficient strength to be machined.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not wilfully added to the composition either as such or in combination with other components or ingredient of other components.

A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably.

The terms "comprise" or "contain" and variations thereof do not have a limiting meaning where these terms appear in the description and claims. "Consisting essentially of" means that specific further components can be present, namely those which do not materially affect the essential characteristic of the article or composition. "Consisting of" means that no further components should be present. The term "comprise" shall include also the terms "consist essentially of" and "consists of".

Also herein, the recitations of numerical ranges by endpoints include all numbers subsumed within that range (e.g., 1 to 5 includes 1, 1.5, 2, 2.75, 3, 3.80, 4.5. etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

DETAILED DESCRIPTION

Meanwhile more and more different workflows for dental zirconia restorations are commercially available where different process parameters are suggested.

These different process parameters often make it difficult to produce the same color under all these different sintering and consecutive firing conditions.

It has been observed that the aesthetics of sintered zirconia material, which contain coloring oxides, can be influenced by varying the sintering speed for the zirconia material to be sintered, in particular if the sintering speed is increased.

The use of a particular combination of coloring oxides in combination with fluorescing oxides was found to be useful for addressing this issue.

The combination of certain coloring oxides and bismuth oxides contained in the zirconia material of a dental mill blank, wherein certain oxides are not present or only present in small amounts as described in the present text does not only facilitate the manufacturing of tooth colored dental restorations, but also gives the tooth colored dental restorations a naturally fluorescent appearance.

Further, it was found that by using a particular combination of oxides, which is essentially free of iron, manganese and also cobalt, it is possible to produce a dental restoration in all desired tooth colors (e.g. according to the Vita™ Tooth Shade Guide) even, if different sintering rates are used.

Without wishing to be bound by a certain theory, it is believed that the combination of oxides described in the present text is sufficiently stable even under very different sintering conditions without showing an undesired discoloration, which was sometimes observed when using other combinations of elements.

The selection of elements suggested in the present text essentially consists of erbium (Er), terbium (Tb), chromium (Cr) and bismuth (Bi). In addition, iron (Fe), manganese (Mn) and cobalt (Co) need to be essentially absent from the zirconia material to be sintered.

Er can be referred to as a red shading component, Tb as a yellow shading component, Cr as a grey shading component and Bi as a fluorescence component.

It was found that Fe, a possible alternative as the yellow shading component, would prevent the fluorescence effect by absorbing all UV radiation that Bi needs for producing fluorescence. It was also observed that Fe may change its oxidation state under certain firing conditions which may lead to a non-desired grey discoloration.

It was also found that Mn, a possible alternative as the grey shading component, has shown that it can influence the oxidation state of Tb. Usually, the use of Mn results in a comparatively low yellow shade, which has to be compensated by adding a higher amount of Tb, which is uneconomic. Also, the use of Mn can lead to a significant variation of the yellow shade under different sintering conditions which is often aesthetically not desired.

It was further found that Co, another possible alternative as the grey shading component, has shown that it does not add a grey shade as effectively as Cr or Mn. Also, the use of Co can lead to a significant variation of the red shade under different sintering conditions which is often aesthetically not desired.

Thus, according to the invention the presence of the oxides of Fe, Mn and Co in the dental mill blank should be avoided or limited.

So far, no combination of elements had been proposed that can provide inherent fluorescence and at the same time a sufficient color stability during different sintering processes.

The combination of elements proposed in the present text enables an inherent tooth-like fluorescence of a zirconia material and the respective dental restoration obtained thereof.

It also enables a more stable color of the dental restoration even if different process parameters were applied during a sintering step compared to the currently used combinations of coloring components.

The dental mill blank described in the present text is also useful for producing a so-called monolithic dental restoration.

Producing a monolithic dental restoration out of a porous zirconia material has to address the need for translucency in the dental appliance, which is usually met by a fluorescing veneering material.

According to the invention, using a fluorescing veneering material is no longer needed. The material the dental milling blank is made of is already fluorescing and the metal oxides contained therein are adapted to enable the production of a dental restoration with the desired tooth color at a high sintering rate.

As mentioned above, this is beneficial especially for producing so called monolithic dental restorations which typically consist essentially of the zirconia material, without the need of veneering material(s).

However, a thin glaze layer, being fluorescent or non-fluorescent, may still be applied to the outer surface of the zirconia to provide surface gloss, if desired. Alternatively, polishing may be conducted to obtain a glossy surface, if desired.

It was also found that dental article(s) machined from the porous zirconia material of the dental mill blank(s) can be sintered to final density very fast without negatively affecting physical and mechanical properties like bending strength and without causing distortion, despite the fact that further oxides are present, which need to diffuse into the crystalline structure of the sintered dental restoration.

One aspect of the invention is directed to a dental mill blank. The dental mill blank comprises or essentially consists of a porous dental zirconia material.

Depending on the mode of production, certain properties of the porous zirconia material of the dental mill blank may vary.

If the porous zirconia material is produced by a pressing technique followed by a heat-treatment step (e.g. pre-sintering step), the porous zirconia material can typically be characterized by the following parameters alone or in combination:

a) average grain size: less than 100 nm or less than 80 nm or less than 60 nm;

b) average connected pore diameter: 10 to 100 nm;

c) BET surface: 2 to 20 $m^2/g$ or 3 to 16 $m^2/g$ or 3 to 14 $m^2/g$;

d) biaxial flexural strength: 8 to 80 or 15 to 55 MPa;

e) Vickers hardness: 25 (HV 0.5) to 150 or 35 to 140 (HV 1).

According to one embodiment, the porous zirconia material may be characterized by the following parameters alone or in combination:

a) average grain size: less than 100 nm;

b) average connected pore diameter: 10 to 100 nm;

c) BET surface: 2 to 20 $m^2/g$;

d) biaxial flexural strength: 8 to 80 MPa;

e) Vickers hardness: 25 (HV 0.5) to 150 (HV 1).

According to another embodiment, the porous zirconia material may be characterized by the following parameters alone or in combination:

a) average grain size: less than 60 nm;

b) average connected pore diameter: 10 to 100 nm;

c) BET surface: 3 to 14 $m^2/g$;

d) biaxial flexural strength: 15 to 55 MPa;

e) Vickers hardness: 35 (HV 0.5) to 140 (HV 1).

Further details of the pressing technique and the subsequent pre-sintering or heat-treatment step are described in the text below. If desired, the respective properties can be determined as described in the example section.

A combination of the parameters a) and b); or a) and c); or a) and d); or a), c) and d) can sometimes be preferred.

It was found that it can be beneficial for certain properties, if the porous zirconia material has a certain BET surface. The BET surface should be in a particular range. It should not be too small and also not be too large.

If the BET surface of the material is too low, it might not be sinter-active enough to reach or to get close to theoretical density during a speed-sintering cycle, which would negatively affect the material strength and translucency.

If the BET surface of the material is too high, it might be difficult to obtain a green body of sufficient density by a pressing step. In this case, it would also be difficult to obtain a material of desired strength and translucency in a subsequent sintering cycle.

The Vickers hardness of the material is typically also in a particular range.

If the Vickers hardness of the material is too low, the machinability could fall off in quality (edge chipping or breaking of the workpiece) as well as in the ease of manual reworking to individualize the frame of a dental restoration or a monolithic restoration as well.

If the Vickers hardness of the material is too high, the wear of the machining tools may increase to an uneconomic range or the tool could break and destroy the workpiece.

The biaxial flexural strength of the material is typically also in a particular range.

It was found that if the biaxial flexural strength of the material is too low, the material tends to crack during the milling process or during the manual finishing by a dental technician.

On the other hand, if the biaxial flexural strength of the material is too high, the processing of the material by a milling machine is often not possible with reasonable effort. The milling tool or the milled material often tend to chip or break. In such a case the shaping of the material would have to be done by grinding, e.g. using a Cerec™ grinding machine (Sirona).

It was found that a porous dental material having the above described features typically exhibits better machinablility and faster sinterability compared to other commercially available dental mill blanks.

Thus, the porous zirconia material described in the present text may have a unique combination of features, which facilitates a reliable production of highly aesthetic dental ceramic articles.

The porous zirconia material of the dental mill blank of the present text comprises or consists essentially of oxides of Zr (typically combined with traces of oxides of Hf), Y, optionally Al, as well as Bi, Tb, Er and Cr.

The oxides of Tb, Er and Cr are typically present in the following amounts:

Tb oxide calculated as $Tb_4O_7$: 0.01 to 0.8 wt. %,

Er oxide calculated as $Er_2O_3$: 0.01 to 3.0 wt. %,

Cr oxide calculated as $Cr_2O_3$: 0.0001 to 0.1 wt. %, wt. % with respect to the weight of the porous zirconia material.

In certain embodiments, the oxides of Tb, Er and Cr are typically present in the following amounts:

Tb oxide calculated as $Tb_4O_7$: 0.02 to 0.8 wt. %,

Er oxide calculated as $Er_2O_3$: 0.02 to 3.0 wt. %,

Cr oxide calculated as $Cr_2O_3$: 0.0001 to 0.08 wt. %, wt. % with respect to the weight of the porous zirconia material.

In certain embodiments, the oxides of Tb, Er and Cr are typically present in the following amounts:

Tb oxide calculated as $Tb_4O_7$: 0.01 to 0.8 wt. %,

Er oxide calculated as $Er_2O_3$: 0.2 to 3.0 wt. %,

Cr oxide calculated as $Cr_2O_3$: 0.0001 to 0.06 wt. %, wt. % with respect to the weight of the porous zirconia material.

In certain embodiments, the oxides of Tb, Er and Cr are typically present in the following amounts:

Tb oxide calculated as $Tb_4O_7$: 0.01 to 0.8 wt. %,

Er oxide calculated as $Er_2O_3$: 0.2 to 1.2 wt. %,

Cr oxide calculated as $Cr_2O_3$: 0.0005 to 0.006 wt. %, wt. % with respect to the weight of the porous zirconia material.

The material of the porous dental zirconia article described in the present text may contain about 3, 4 or 5 mol % yttria. These materials are sometimes referred to as 3Y-TZP, 4Y-TZP or 5-YTZP materials. The use of a 4 mol % yttria containing zirconia material is sometimes preferred.

The oxides of Tb, Er and Cr are typically the only oxides which significantly contribute to the color of the zirconia material after sintering.

The porous zirconia material does not comprise

Fe oxide calculated as $Fe_2O_3$ of more than 0.01 wt. %, or more than 0.003 wt. %, Mn oxide calculated as $MnO_2$ of more than 0.005 wt. %, or more than 0.003 wt. %, Co oxide calculated as $Co_2O_3$ of more than 0.005 wt. %, or more than 0.003 wt. %, wt. % with respect to the weight of the porous zirconia material.

It can be preferred that there is no or essentially no iron present at all. Thus, the zirconia material is essentially free of iron. However, sometimes due to production processes and raw materials used, it is unavoidable that traces of iron are still present in the material.

If, however, the content of iron (calculated as oxide) is above the ranges described in the present text, the desired naturally fluorescent appearance of the dental article cannot be properly achieved.

Without wishing to be bound to a certain theory, it is believed that by using iron as coloring agent, either the UV light needed to initiate the fluorescence or the emitted blue fluorescence light itself or even both are being absorbed by the iron and thus lost for the desired visual appearance.

Mn and Co on the other hand, do not show this behaviour and do not prevent fluorescence, but they do not provide the same color stability as Cr. Therefore, like iron, the zirconia material is also essentially free of Mn and Co.

The porous zirconia material typically comprises the respective oxides in the following amounts:

Zr oxide calculated as $ZrO_2$: 85 to 96 wt. %,

Y oxide calculated as $Y_2O_3$: 3 to 15 wt. %,

Al oxide calculated as $Al_2O_3$: 0 to 0.15 wt. %,

Bi oxide calculated as $Bi_2O_3$: 0.01 to 0.2 wt. %,

Tb oxide calculated as $Tb_4O_7$: 0.01 to 0.8 wt. %,

Er oxide calculated as $Er_2O_3$: 0.01 to 3.0 wt. %,

Cr oxide calculated as $Cr_2O_3$: 0.0001 to 0.1 wt. %, wherein the following oxides are not present Fe oxide calculated as $Fe_2O_3$ in an amount of more than 0.01 wt. %, Mn oxide calculated as $MnO_2$ in an amount of more than 0.005 wt. %, Co oxide calculated as $Co_2O_3$ in an amount of more than 0.005 wt. %, wt. % with respect to the weight of the porous zirconia material.

Thus, the porous zirconia material is essentially free of oxides of Fe, Mn and Co. That is, these oxides are not wilfully added.

According to a further embodiment, the porous zirconia material is also essentially free of either one or some or all of the following oxides: oxides of Dy, Sm, Nd, Cu, V, Mo, Ni or mixtures thereof.

That is, these oxides are typically not present at all.

The presence of each of these oxides up to 0.01 wt. % or up to 0.005 wt. % or up to 0.001 wt. % with respect to the weight of the porous zirconia material may, however, be allowed and can sometimes not be avoided due to traces being present in the raw materials used.

If traces are present, they are typically present in the following amounts:

Dy oxide calculated as $Dy_2O_3$: up to 0.01 wt. % or up to 0.001 wt. %,

Sm oxide calculated as $Sm_2O_3$: up to 0.01 wt. % or up to 0.001 wt. %,

Nd oxide calculated as $Nd_2O_3$: up to 0.01 wt. % or up to 0.001 wt. %,

Eu oxide calculated as $Eu_2O_3$: up to 0.01 wt. % or up to 0.001 wt. %,

Cu oxide calculated as CuO: up to 0.01 wt. % or up to 0.001 wt. %,

V oxide calculated as $V_2O_5$: up to 0.01 wt. % or up to 0.001 wt. %,

Mo oxide calculated as $Mo_2O_3$: up to 0.01 wt. % or up to 0.001 wt. %,

Ni oxide calculated as NiO: up to 0.01 wt. % or up to 0.001 wt. %, wt. % with respect to the weight of the porous zirconia material.

Further, the porous zirconia material does typically also not comprise glass, glass ceramic or a lithium (di)silicate ceramic in an amount above 1 wt. % with respect to the weight of the porous zirconia material.

The dental mill blank may also be characterized by its shape and/or size.

The dental mill blank has a shape allowing the mill blank to be reversibly attached or fixed to a machining device. Suitable shapes include discs or blocks (e.g. cubic, cuboid, cylinder, etc.).

For a cubic or cuboid shaped blank, typical dimensions are at least 19 mm in 2 dimensions, and at least 12 mm in the third dimension.

Alternatively, a porous zirconia dental mill blank having the shape of a block may have the following dimensions: x-dimension: 12 to 45 mm, or 19 to 40 mm; y-dimension: 12 to 70 mm, or 19 to 60 mm; z-dimension: 10 to 40 mm, or 12 to 25 mm.

For a cylindric or disc shaped block, typical dimensions are more than 19 mm in diameter, more than 12 mm in height.

Alternatively, a porous zirconia dental mill blank having the shape of a disc may have the following dimensions: x, y-dimension: 90 to 110 mm, or 95 to 105 mm; z-dimension: 10 to 35 mm, or 12 to 30 mm. The dental mill blank may also comprise means for attaching the dental mill blank to a machining device.

Suitable means include frame(s), notch(es), stub(s), mandrels and combinations thereof.

Fixing of the dental zirconia mill blank to such a means can be affected by clamping, gluing, screwing and combinations thereof. Using such a means may facilitate the production of the dental restoration with a machining device.

Examples of holding devices or means are described e.g. in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The porous zirconia material of the dental mill blank can be produced by different methods.

According to one embodiment, the process of producing the dental mill blank comprises the steps of:

providing a porous zirconia material and a coloring solution, the porous zirconia material comprising Zr oxide, Y oxide and optionally Al oxide, the coloring solution comprising a solvent (e.g. water) and ions of Tb, Er and Cr, either the porous zirconia material or the coloring solution or the porous zirconia material and the coloring solution comprising Bi, treating the porous zirconia material with the coloring solution, optionally applying a drying step.

The composition of the porous zirconia material and the coloring solution are adjusted so that after the treatment, the porous zirconia material does not comprise Fe calculated as Fe oxide in an amount of more than 0.01 wt. %, Mn and Co calculated as oxides each in an amount of more than 0.005 wt. %.

That is, if desired, the dental mill blank can be produced by treating a porous zirconia material with a coloring solution containing certain coloring ions.

Alternatively, the dental mill blank can be produced by a process comprising the steps of providing a zirconia powder comprising Tb oxide providing a zirconia powder comprising Er oxide, providing a zirconia powder comprising Cr oxide, providing a zirconia powder comprising Bi oxide, providing a zirconia powder not comprising oxides of Tb, Er, Cr and Bi, mixing and/or layering the zirconia powders described above, compacting the layered and/or mixed zirconia powders, optionally applying a heat-treatment step, the zirconia powder comprising Zr oxide, Y oxide and optionally Al oxide, none of the zirconia powders or the dental mill blank comprising Fe oxide in an amount of more than 0.01 wt. %, Mn and Co oxides each in an amount of more than 0.005 wt. %.

That is the dental mill blank can be produced by using different zirconia powders and mixing and/or layering them in the desired order.

The respective zirconia powders typically contain the additional oxides in the following amounts:

zirconia powder comprising Tb oxide in an amount of 0.5 to 6.0 wt. %, providing a zirconia powder comprising Er oxide in an amount of 0.5 to 12.0 wt. %, providing a zirconia powder comprising Cr oxide in an amount of 0.01 to 0.5 wt. %, providing a zirconia powder comprising Bi oxide in an amount of 0.01 to 0.8 wt. %, wt. % with respect to the zirconia powder.

The mean particle size of the zirconia powders is typically in a range of 20 to 100 μm.

Generally, the porous zirconia material of the dental mill blank can be obtained by a process comprising the steps of mixing the powders of the respective oxides contained in the material to obtain a powder mixture, pressing the powder mixture, and optionally heat-treating the pressed powder mixture.

Generally, the individual powders can be obtained by a process comprising the steps of treating a zirconia powder with a solution containing metal ions selected from Bi, Tb, Er and/or Cr, drying the mixture to obtain a powder.

Alternatively, the individual powders can be obtained by a process comprising the steps of treating a zirconia powder with a powder containing metal oxides selected from Bi, Tb, Er and/or Cr, milling the mixture in wet state, (spray-)drying the mixture to obtain a powder.

Suitable zirconia powders are commercially available from various sources including Tosoh Company (Japan).

Mixing of the powders can be achieved by shaking the powders or putting the powders in a mill (e.g. ball mill, attritor mill) and milling the powders until a homogenous powder mixture is obtained. Further possible mixing equipment can include sieves or granulators.

To facilitate the pressing or compacting step(s), pressing aids can be added, if desired.

Suitable pressing aids include binders, lubricating additives and mixtures thereof.

If desired, these aids can be added to the zirconia oxide powder being the main component of the powder mixture.

The powder mixture is then placed in a mould and pressed into the shape of a dental mill blank.

The pressure to be applied is typically in the range of 150 to 300 MPa. Alternatively, the applied pressure is set so that the pressed ceramic body reaches a certain density, e.g. in the case of zirconia ceramic a density of 2.8 $g/cm^3$ to 3.5 $g/cm^3$.

If desired, a calcining step can be done.

In a further step, a heat treatment is applied to the compacted composition to obtain a porous dental mill blank.

The temperature of the heat treatment is typically in a range of 800 to 1,100° C. or 900 to 1,000° C.

The heat treatment is typically applied for a duration of 10 to 70 hours or 15 to 60 hours.

The article obtained after heat treatment can be machined or sectioned into any desired shape.

The invention is also directed to a process of producing a dental restoration.

Such a process typically comprises the following steps:

providing a dental mill blank comprising a porous zirconia material as described in the present text or obtained according to a process as described in the present text, machining a dental restoration out of the porous zirconia material, sintering the dental restoration.

The machining step is typically done with or by using a milling or grinding device. Those devices are commercially available e.g. from Roland (DWX mills), or Sirona (CEREC™ inLab CAD/CAM) or others.

The machining step can be done with a milling, drilling, cutting, carving, or grinding device.

Useful milling parameters include:

rotary speed of milling tool: 5,000 to 40,000 revolutions/min;

feed rate: 20 to 5,000 mm/min;

milling cutter diameter: 0.8 to 4 mm.

If desired, the machined porous dental zirconia restoration is cleaned, e.g. by removing milling dust with pressurized air.

The process of producing the dental restoration comprises a sintering step.

The sintering will result in a zirconia dental article, sometimes also referred to as crystalline metal oxide article.

If conducted, the firing or sintering step should be accomplished under conditions which results in a dental ceramic article having an acceptable tooth-like color (e.g. a color which fits the Vita™ shade system).

Useful sintering conditions can generally be characterized by the following parameters alone or in combination:

temperature: 1,100 to 1,600° C. or 1,100 to 1,500° C. or 1,100° C. to 1,450° C. or 1,100° C. to 1,300° C. or 1,300° C. to 1,600° C. or 1,400° C. to 1,580° C. or 1,450° C. to 1,580° C.;

atmosphere: air or inert gas (e.g. nitrogen, argon);

duration: until a density of at least 98 or 99 to 100% of the theoretically achievable density of the material has been reached;

dwell time: 0 to 24 h or 0.1 to 5 h;

pressure: ambient pressure.

According to one embodiment, the sintering condition are characterized as follows: temperature: 1,100 to 1,600° C.;

atmosphere: air; duration: until a density of at least 98 of the theoretically achievable density of the material has been reached; dwell time: 0 to 24 h.

During the firing process the porous dental article is sintered to its final shape, thereby undergoing changes with regard to dimension, density, hardness, bending strength and/or grain size.

The dwell time (that is the time during which the article is kept at the sintering temperature) is not critical. The dwell time can be zero. The dwell time, however, can also be in a range of 0 to 24 h or 0.1 to 5 h.

The sintering temperature and dwell time are, however, typically correlated. A higher temperature typically requires a shorter dwell time.

Thus, the dwell time, may last from 0 to 5 h (e.g. if the firing temperature is 1,550° C.) or from 0.1 to 24 h (e.g. if the firing temperature is 1,100° C.).

Generally, the sintering or firing conditions are adjusted such that the sintered dental ceramic article has a density of equal or greater than 98% compared with the theoretically achievable density.

If a faster processing is desired, higher heating rates can be used.

Generally, useful heat-treating conditions for so-called speed or fast sintering can be characterized by the following features alone or in combination:
- a) heating rate: 1.5 to 7° C./sec or 2 to 7° C./sec or 3 to 7° C./sec;
- b) sintering temperature: at least 1,400° C. or at least 1,450° C. or at least 1,500° C.;
- c) atmosphere: air or inert gas (e.g. nitrogen, argon);
- d) duration: less than 60 min;
- e) dwell time: 0 to 10 min;
- f) pressure: ambient pressure.

According to one embodiment suitable heat-treating conditions are characterized by the following features alone or in combination:
- a) heating rate: 2 to 7° C./sec;
- b) sintering temperature: at least 1,500° C.;
- c) atmosphere: air;
- d) duration: less than 60 min;
- e) dwell time: 0 to 10 min;
- f) pressure: ambient pressure.

A combination of the following features is sometimes preferred: a) and b); a), b) and d); a), b), c), d) and e).

An oven which can be used for the process described in the present text is commercially available from Dentsply Sirona (SpeedFire™)

A suitable furnace is also described in WO 2017/144644 A1 (Sirona). This furnace is for carrying out a heat treatment of a dental replacement part and comprises an induction coil, a radiant heater, an insulation layer and a furnace chamber. Further, the furnace has a cooling system to control the internal temperature of the furnace chamber.

Alternatively to the fast heat treatment process where high heating rates are used, the sintering process can also be conducted by using lower heating rates.

A respective sintering protocol can be characterized as follows:
- heating rate: 1 to 60° C./min;
- sintering temperature: 1,100 to 1,600° C.;
- duration: 60 to 480 min.

A furnace which can be used is the commercially available Lava™ Furnace 200 (3M Oral Care).

The invention is also directed to the dental restoration obtainable or obtained by the process described in the present text.

The dental restoration may have the shape of a crown, bridge, inlay, onlay, veneer, facing, coping, crown and bridge framework, implant, abutment, orthodontic appliances (e.g. brackets, buccal tubes, cleats and buttons) and parts thereof.

The dental mill blank described in the present text can particularly be used for producing monolithic dental restorations.

After the sintering step the material of the dental restoration can usually be characterized by the following features alone or in combination:
- a) density: at least 98% of theoretical density;
- b) phase content
  tetragonal phase: 20 to 90 wt. % or 30 to 80 wt. %;
  cubic phase: 10 to 80 wt. % or 20 to 70 wt. %;
- c) biaxial flexural strength: 450 MPa to 2,200 MPa, or 500 MPa to 2,000 MPa;
- d) translucency: at least 15% determined on a sample having a thickness of 1 mm in reflection mode, averaged over the wavelengths from 400 to 700 nm.

According to one embodiment, after the sintering step the material of the dental restoration is characterized by the following features alone or in combination:
- a) density: at least 98% of theoretical density;
- b) phase content
  tetragonal phase: 30 to 80 wt. %;
  cubic phase: 20 to 70 wt. %;
- c) biaxial flexural strength: 500 MPa to 2,000 MPa;
- d) translucency: at least 15% determined on a sample having a thickness of 1 mm in reflection mode, averaged over the wavelengths from 400 to 700 nm.

A combination of the features a) and b); or a) and c); or a) and d); or a), b), c); or a), b) and d) can sometimes be preferred.

The properties are typically determined on test samples having the same material properties as the material the dental restoration is made of but having an appropriate size or dimension.

The invention is also directed to a kit of parts.

The kit of parts comprises
the dental mill blank comprising a porous zirconia material as described in the present text,
a dental cement.

The dental cement is used for attaching or fixing a dental restoration machined out of the dental mill blank to a tooth surface.

Suitable dental cements include resin-modified glass ionomer (RM-GIZ) cements and also self-adhesive resin cements.

RM-GIZ cements typically contain an acid-reactive filler (such as a fluoro aluminosilicate glass), water, optionally polyacid, polymerizable components (such as (meth)acrylate components), and an initiator system.

Self-adhesive resin cements typically contain an acidic polymerizable component (e.g. a (meth)acrylate component bearing a phosphoric or carboxylic acid moiety), polymerizable components without an acidic moiety, an initiator system, and filler.

Suitable dental cements are also commercially available, such as RelyX™ Unicem 2 or RelyX™ Luting Plus (3M Oral Care)

The kit of parts described in the present text may further comprise the following components alone or in combination:
instruction for use;
sintering furnace.

The instruction for use typically contain information on machining processes and parameters to be applied as well as sintering conditions useful for sintering the machined article to final density as described in the present text.

The sintering furnace can be a furnace for conducting a regular sintering process or for conducting a speed-sintering process.

Sintering devices as described in the present text can be used. Sintering furnaces are also commercially available, e.g. from 3M Oral Care, DentsplySirona, or Ivoclar.

The invention is also directed to the use of the combination of the elements of Tb, Er, Cr and Bi without the use of the elements of Mn, Fe and Co for producing a dental zirconia restoration or a dental mill blank comprising Zr oxide, Y oxide and optionally Al oxide in particular as described in the present text.

This use is particularly suitable for the production of a dental zirconia restoration where a fast or speed-sintering process as described in the present text is applied.

The method for producing a dental mill blank described above where a porous zirconia is treated with a coloring solution can similarly be applied to a dental zirconia restoration.

In this respect, the dental zirconia restoration is machined out of a dental mill blank comprising a porous zirconia material, which is typically non-colored. The dental zirconia restoration is then treated with a coloring solution comprising a solvent (e.g. water) and the coloring ions Tb, Er and Cr in combination and Bi as fluorescing agent in addition, if desired. Ions selected from Fe, Mn and Co alone or in combination are not present, especially not present in an amount which would be detrimental to the result to be achieved.

The volume and the concentration of the ions in the coloring solution is typically adjusted to the porous zirconia material of the dental restoration so that in the sintered dental restoration the concentration of the respective oxides is in the range described in the present text.

As an example, the concentration of the respective ions in the coloring solution is typically in the following range: Tb: 0.05 to 4.0 wt. %, Er: 0.05 to 15.0 wt. %, Cr: 0.0005 to 0.5 wt. %, and optionally Bi: 0.05 to 1.0 wt. %, with respect to the weight of the coloring solution.

Other suitable embodiments of the invention include:

Embodiment 1

A dental mill blank comprising a porous zirconia material, the dental mill blank being characterized as follows:

having the shape of a cubic, cylinder or disc, comprising means for attaching the dental mill blank to a machining device, the porous zirconia material being characterized as follows:

BET surface: 2 to 20 $m^2/g$;

biaxial flexural strength: 8 to 80 MPa;

x, y dimension: at least 19 mm;

z dimension: at least 12 mm;

Density: 30 to 95% of theoretical density;

the porous zirconia material comprising:

Zr oxide calculated as $ZrO_2$: 80 to 96 wt. %,

Al oxide calculated as $Al_2O_3$: 0 to 0.15 wt. %,

Y oxide calculated as $Y_2O_3$: 3 to 15 wt. %,

Bi oxide calculated as $Bi_2O_3$: 0.01 to 0.2 wt. %,

Tb oxide calculated as $Tb_4O_7$: 0.01 to 0.8 wt. %,

Er oxide calculated as $Er_2O_3$: 0.01 to 3.0 wt. %,

Cr oxide calculated as $Cr_2O_3$: 0.0001 to 0.1 wt. %, the porous zirconia material not comprising:

Fe oxide calculated as $Fe_2O_3$ in an amount of more than 0.01 wt. %,

Mn oxide calculated as $MnO_2$ in an amount of more than 0.005 wt. %,

Co oxide calculated as $Co_2O_3$ in an amount of more than 0.005 wt. %, a glass, glass ceramic or lithium disilicate material, wt. % with respect to the weight of the porous zirconia material.

Embodiment 2

A dental mill blank comprising a porous zirconia material, the dental mill blank being characterized as follows:

having the shape of a cube, rectangular prism, cylinder or disc, comprising means for attaching the dental mill blank to a machining device, the porous zirconia material being characterized as follows:

BET surface: 2 to 20 $m^2/g$;

biaxial flexural strength: 8 to 80 MPa;

x, y dimension: at least 19 mm;

z dimension: at least 12 mm;

Density: 30 to 95% of theoretical density;

the porous zirconia material comprising:

Zr oxide calculated as $ZrO_2$: 80 to 96 wt. %,

Al oxide calculated as $Al_2O_3$: 0 to 0.15 wt. %,

Y oxide calculated as $Y_2O_3$: 3 to 15 wt. %,

Bi oxide calculated as $Bi_2O_3$: 0.01 to 0.2 wt. %,

Tb oxide calculated as $Tb_4O_7$: 0.01 to 0.8 wt. %,

Er oxide calculated as $Er_2O_3$: 0.01 to 3.0 wt. %,

Cr oxide calculated as $Cr_2O_3$: 0.0001 to 0.1 wt. %, the porous zirconia material not comprising:

Fe oxide calculated as $Fe_2O_3$ in an amount of more than 0.01 wt. %,

Mn oxide calculated as $MnO_2$ in an amount of more than 0.005 wt. %,

Co oxide calculated as $Co_2O_3$ in an amount of more than 0.005 wt. %, a glass, glass ceramic or lithium disilicate material, wt. % with respect to the weight of the porous zirconia material.

Embodiment 3

A dental mill blank comprising a porous zirconia material, the dental mill blank being characterized as follows:

having the shape of a cube, rectangular prism, cylinder or disc, comprising means for attaching the dental mill blank to a machining device, the porous zirconia material being characterized as follows:

BET surface: 2 to 20 $m^2/g$;

biaxial flexural strength: 8 to 80 MPa;

x, y dimension: at least 19 mm;

z dimension: at least 12 mm;

Density: 30 to 95% of theoretical density;

the porous zirconia material comprising:

Zr oxide calculated as $ZrO_2$: 80 to 96 wt. %,

Al oxide calculated as $Al_2O_3$: 0 to 0.15 wt. %,

Y oxide calculated as $Y_2O_3$: 3 to 15 wt. %,

Bi oxide calculated as $Bi_2O_3$: 0.01 to 0.2 wt. %,

Tb oxide calculated as $Tb_4O_7$: 0.01 to 0.8 wt. %,

Er oxide calculated as $Er_2O_3$: 0.01 to 3.0 wt. %,

Cr oxide calculated as $Cr_2O_3$: 0.0001 to 0.1 wt. %,
the porous zirconia material not comprising:
  Fe oxide calculated as $Fe_2O_3$ in an amount of more than 0.01 wt. %,
  Mn oxide calculated as $MnO_2$ in an amount of more than 0.005 wt. %,
  Co oxide calculated as $Co_2O_3$ in an amount of more than 0.005 wt. %,
  V oxide calculated as $V_2O_5$: in an amount of more than 0.01 wt. %,
  a glass, glass ceramic or lithium disilicate material,
wt. % with respect to the weight of the porous zirconia material.

Embodiment 4

A dental mill blank comprising a porous zirconia material, the dental mill blank being characterized as follows:
  having the shape of a cubic, cylinder or disc,
  comprising means for attaching the dental mill blank to a machining device,
the porous zirconia material being characterized as follows:
  BET surface: 2 to 20 $m^2/g$;
  biaxial flexural strength: 8 to 80 MPa;
  x, y dimension: at least 19 mm;
  z dimension: at least 12 mm;
  Density: 30 to 95% of theoretical density;
the porous zirconia material comprising:
  Zr oxide calculated as $ZrO_2$: 80 to 96 wt. %,
  Al oxide calculated as $Al_2O_3$: 0 to 0.15 wt. %,
  Y oxide calculated as $Y_2O_3$: 3 to 15 wt. %,
  Bi oxide calculated as $Bi_2O_3$: 0.01 to 0.2 wt. %,
  Tb oxide calculated as $Tb_4O_7$: 0.01 to 0.8 wt. %,
  Er oxide calculated as $Er_2O_3$: 0.2 to 1.2 wt. %,
  Cr oxide calculated as $Cr_2O_3$: 0.0005 to 0.006 wt. %,
the porous zirconia material not comprising:
  Fe oxide calculated as $Fe_2O_3$ in an amount of more than 0.01 wt. %,
  Mn oxide calculated as $MnO_2$ in an amount of more than 0.005 wt. %,
  Co oxide calculated as $Co_2O_3$ in an amount of more than 0.005 wt. %,
  a glass, glass ceramic or lithium disilicate material,
wt. % with respect to the weight of the porous zirconia material.

All components used in the dental composition of the invention should be sufficiently biocompatible, that is, the composition should not produce a toxic, injurious, or immunological response in living tissue.

The dental articles described in the present text do typically not contain components or additives which jeopardize the intended purpose to be achieved with the invention. Thus, components or additives added in an amount which finally results in a non-tooth-colored dental article are usually not contained in the dental article. Typically, an article is characterized as not being tooth colored if it cannot be assigned a color from the Vita™ color code system, known to the person skilled in the art. Additionally, components which will reduce the mechanical strength of the dental restoration to a degree, where mechanical failure will occur, are usually also not included in the dental article.

Further, the producing of the zirconia material described in the present text does typically also not require the application of a hot isostatic pressing step (HIP).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized (DI) water, and all molecular weights are weight average molecular weight. Moreover, unless otherwise indicated all experiments were conducted at ambient conditions (23° C.; 1013 mbar).

Methods

Elemental Composition

If desired, the elemental composition can be determined by X-ray fluorescence spectrometry (XRF), e.g. with the ZSX Primus II from Rigaku, Japan. This method is especially suited for the analysis of solids, e.g. zirconia ceramics or glass materials.

Average Connected Pore Diameter

If desired, the average connected pore diameter can be determined as follows: Mercury is introduced in the porous material under high pressure using a porosimeter (Quantachrome Poremaster). The applied pressure is related to pore size by the opposing force of the surface tension of Mercury. Using the so-called Washburn equation, the average connected pore diameter can be determined. The following measurement parameters are applied or used for result calculation: Pressure range from 20 to 60000 PSIA, temperature during measurement 20° C., Hg Contact Angle 140° and Hg Surface Tension 480 mN/m.

Porosity

If desired, the porosity can be determined as follows: Porosity=(1−(density of porous material/density of sintered material))×100. The density of the porous material can be calculated by the division of weight and volume. Volume can be obtained by geometrical measurements.

Average Grain Size of Sintered Body

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Mean Particle Size of Powder Composition

If desired, the mean particle size of the particles of the zirconia powders can be determined by light scattering techniques, e.g. with a Mastersizer 3000 from Malvern Panalytical.

Biaxial Flexural Strength

If desired, the biaxial flexural strength of pre-sintered material can be determined according to ISO 6872 with the following modifications: The pre-sintered sample is sawn into wafers with a thickness of 2+/−0.1 mm using a dry cut saw. The diameter of the samples should be 17+/−2 mm. The parallel large faces of the wafer are ground using silicon carbide sand paper (P2500). Each wafer is centred on a support of three steel balls (diameter of the balls 6 mm) with a support diameter of 14 mm. The punch diameter in contact with the wafer is 3.6 mm. The punch is pushed onto the wafer at a rate of 0.1 mm per min. A minimum of 15 samples is measured to determine the average strength. The tests can be conducted in an Instron 5566 universal testing machine (Instron Deutschland GmbH).

Vickers Hardness

If desired, the Vickers hardness can be determined according to ISO 14705 with the following modifications: The surface of the pre-sintered samples is ground using silicon carbide sand paper (P2500). The surface of the sintered samples is polished with 20 μm diamond suspension. The test forces are adjusted to the hardness level of samples. Used test forces are between 0.2 kg and 2 kg and are applied for 15 s each indentation. A minimum of 10 indentations is measured to determine the average Vickers hardness. The tests can be conducted with a hardness tester Leco M-400-G (Leco Instrumente GmbH).

Density

If desired, the density of the sintered material can be measured by an Archimedes technique. The measurement is made on a precision balance using a density determination kit (identified as "YDK01" from Sartorius AG). In this procedure, the sample is first weighed in air (A), then immersed in a solution (B). The solution is a 0.05 wt. % tenside solution (e.g. "Berol 266, Fa. Hoesch) in de-ionized water. The density is calculated using the formula $\rho=(A/(A-B))\rho0$, where $\rho0$ is the density of water. The relative density can be calculated by reference to the theoretical density ($\rho t$) of the material, $\rho_{rel}=(\rho/\rho t)100$.

Crystalline Phase Content

If desired, the phase content can be determined by x-ray diffraction (XRD) using a BrukerD8 Discover device (Bruker AXS) and the TOPAS™ software provided by the manufacturer (Bruker) applying the Rietveld analyses and using the Bragg-Brentano geometry. The phase content calculated by the TOPAS™ software is given in wt. %. The measurement is typically performed down to a depth of 3 to 6 μm, which is approximately the penetration depth of x-rays in zirconia.

BET Surface

If desired, the BET surface of a porous article can be determined as follows: Total pore volume and average pore diameter can be analyzed with the use of $N_2$ sorption isotherms and BET surface area analysis. Samples of around 0.1-2 grams were cut, if necessary, from larger samples in order to be inserted in to the straight tubes testing of the instrument. All samples are degassed in vacuum for more than 1 h at 120° C. before analysis. The samples are then analyzed by adsorption and desorption of $N_2$ gas with a Belsorb II (distributed by Robotherm Präzisionsmesstechnik, Bochum, Germany) in a 9 mm cell with 2 cm bulb and with a 5 mm glass rod. At temperature of liquid nitrogen, absorption data points are collected from 0.1 to 0.99 p/p0 and desorption points collected from 0.99 to 0.5 p/p0. The specific surface area S is calculated by the BET method at p/p0 0.25-0.3 (Details regarding calculation see Belsorb Analysis Software User Manual Operating Manual, Chapter 12, Bel Japan. INC).

Fluorescence

If desired, the samples are placed in an UV-light box used for inspection of e.g. thin layer chromatography plates. Fluorescence can be detected by the human eye by the lighting up of the sample against the black background.

Method for Measuring Translucency

If desired, the translucency of the ceramic articles can be evaluated with the following procedure: A test piece in the shape of a disc with an approximate thickness of 1±0.05 mm and an area of measurement of at least 10 mm in diameter is provided. For preparation of the test pieces a pre-sintered block-shaped sample is sawn into wafers with a thickness of approximately 1.3 mm using a dry cut saw. The parallel large faces of the wafer are ground using silicon carbide sand paper (P2500). Alternatively, disc-shaped samples can also be produced during the pressing step, which eliminates the need for sawing and grinding. The samples are sintered in an appropriate furnace to a sintered sample with a thickness of 1±0.05 mm. The sintered sample is measured as fired with a spectrophotometer (X-Rite Color i7, Grand Rapids, USA) in reflectance mode against a white and a black background to obtain the opacity (contrast ratio) of the material, which is an average value over the wavelengths from 400 to 700 nm. The translucency T is calculated according to T=100%−opacity (in percent). Higher values of translucency are indicative of greater transmission of light, and less opacity.

Color

If desired, L*a*b* values can be determined using the same equipment which is used for determining the opacity (contrast ratio) and translucency.

Materials

TABLE 1

| | |
|---|---|
| ZRO2-A | Bindered zirconia powder<br>$ZrO_2 + HfO_2$: 92.8 wt. %; $Y_2O_3$: 7.1 wt. %; $Al_2O_3$: 0.1 wt. % |
| ZRO2-B (Er) | Bindered, erbium oxide containing zirconia powder<br>$ZrO_2 + HfO_2$: 90.8 wt. %; $Y_2O_3$: 0.0 wt. %; $Al_2O_3$: 0.1 wt. %; $Er_2O_3$: 9.1 wt. % |
| ZRO2-C (Tb) | Bindered, terbium oxide containing zirconia powder<br>$ZrO_2 + HfO_2$: 92.4 wt. %; $Y_2O_3$: 5.5 wt. %; $Al_2O_3$: 0.1 wt. %; $Tb_4O_7$: 2.0 wt. % |
| ZRO2-D (Cr) | Bindered, chromium oxide containing zirconia powder<br>$ZrO_2 + HfO_2$: 92.7 wt. %; $Y_2O_3$: 7.1 wt. %; $Al_2O_3$: 0.1 wt. %; $Cr_2O_3$: 0.1 wt. % |
| ZRO2-E (Mn) | Bindered, manganese oxide containing zirconia powder<br>$ZrO_2 + HfO_2$: 94.2 wt. %; $Y_2O_3$: 5.65 wt. %; $Al_2O_3$: 0.1 wt. %; $MnO_2$: 0.05 wt. % |
| ZRO2-F (Co) | Bindered, cobalt oxide containing zirconia powder<br>$ZrO_2 + HfO_2$: 90.7 wt. %; $Y_2O_3$: 9.21 wt. %; $Al_2O_3$: 0.05 wt. %; $Co_2O_3$: 0.04 wt. % |
| ZRO2-G (Bi) | Bindered, bismuth oxide containing zirconia powder<br>$ZrO_2 + HfO_2$: 89.6 wt. %; $Y_2O_3$: 9.8 wt. %; $Al_2O_3$: 0.1 wt. %; $Bi_2O_3$: 0.5 wt. % |

General Procedure for Producing Individual Zirconia Powders

ZRO2-D(Cr) was produced by mixing commercially available zirconia powder with chromium(III) oxide powder ($Cr_2O_3$, e.g. from Aldrich, article no. 769533). The amount of chromium oxide powder was 0.1 wt. % of the mixture. To the mixture, zirconia beads (2 mm diameter, amount: 50% of the weight of the mixture) were added. Mixing was performed with a lab scale powder mixing device (rolling in a jar for 24 hours). The resulting material was homogeneous to the eye and showed very diluted the color of chromium (III) oxide.

General Procedure for Producing Mixed Zirconia Powders

Mixed powders were produced by combination of five of the raw materials from Table 1 (ZRO2-A and ZRO2-B (Er) and ZRO2-C (Tb) and ZRO2-G (Bi) and ZRO2-D (Cr) or ZRO2-E (Mn) or ZRO2-F (Co)) in the desired amounts and shaking the mixture with a lab mixing device (Minishaker MS2 from IKA) until a homogeneous mixture is obtained.

General Procedure for Producing Dental Zirconia Mill Blanks

Samples were produced by using the above described zirconia materials.

The following steps were applied:

Mixing five of the zirconia powders to a powder composition;

Filling the powder composition in a mould (diameter: 24.9 mm);

Applying pressure (97 kN) to the powder filling;

Demoulding the compacted body;

Applying a heat treatment 960° C. for about 1 hour.

The samples were of approximately 1.3 mm in thickness. After sintering, the sample dimensions were adequate for color measurements.

The following samples were prepared:

Sinter Protocol-Fast 2 (SP-F2)
(conducted with a Programat™ CS4 furnace from Ivoclar Vivadent)
RT to 900° C.; 2.2° C./s,
900° C. to 1,500° C.; 0.8° C./s,
1,500° C. to 1,565° C.; 0.3° C./s,
1,565° C.; 240 sec hold,
1,565° C. to 1,200° C.; −1.2° C./s,
1,200° C. to 1,000° C.; −0.8° C./s.

This sintering cycle with a duration of approximately 37 min is a speed-sintering cycle as described in the present text.

Sinter Protocol-Regular 1 (SP-R1)
(conducted with a Programat™ 51 furnace from Ivoclar Vivadent)
RT to 700° C.; 1.2° C./s,
700° C.; 120 sec hold,
700° C. to 1,300° C.; 0.8° C./s,
1,300° C.; 120 sec hold,
1,300° C. to 1,530° C.; 0.7° C./s,
1,530° C.; 1500 sec hold,
1,530° C. to 1,100° C.; −0.7° C./s
1,100° C. to 900° C.; −0.8° C./s.

This sintering cycle with a duration of approximately 70 min is a regular sintering cycle as described in the present text.

Sinter Protocol-Regular 2 (SP-R2)
(conducted with a Lava™ Furnace 200 from 3M Oral Care)
RT to 900° C.; 0.7° C./s,
900° C. to 1,200° C.; 0.3° C./s,

TABLE 2

| | amounts of oxides, given in wt.-%. | | | | | | | | |
|---|---|---|---|---|---|---|---|---|
| Sample | ZrO$_2$/HfO$_2$ | Y$_2$O$_3$ | Al$_2$O$_3$ | Bi$_2$O$_3$ | Tb$_4$O$_7$ | Er$_2$O$_3$ | Cr$_2$O$_3$ | MnO$_2$ | Co$_2$O$_3$ |
| Chromium | 92.390 | 6.557 | 0.100 | 0.032 | 0.059 | 0.858 | 0.004 | — | — |
| Manganese* | 92.503 | 6.434 | 0.100 | 0.032 | 0.060 | 0.867 | — | 0.004 | — |
| Cobalt** | 92.190 | 6.771 | 0.095 | 0.032 | 0.059 | 0.849 | — | — | 0.004 |

General Procedure for Sintering

For sintering the samples obtained from the dental mill blanks the following conditions were applied:

Sinter Protocol-Fast 1 (SP-F1)
(conducted with a SpeedFire™ furnace from Dentsply Sirona)
RT to 400° C.; 4.7° C./s,
400° C. to 1,350° C.; 5.3° C./s,
1,350° C. to 1,580° C.; 4.2° C./s,
1,580° C.; 120 sec hold,
1,580° C. to 1,000° C.; −3.2° C./s,
1,000° C. to 950° C.; −0.3° C./s.

This sintering cycle with a duration of approximately 20 min is a speed-sintering cycle as described in the present text.

1,200° C. to 1,500° C.; 0.3° C./s,
1,500° C.; 1,800 sec hold,
1,530° C. to 1,000° C.; −0.3° C./s
1,000° C. to 400° C.; −1.0° C./s.

This sintering cycle with a duration of approximately 130 min is a regular sintering cycle as described in the present text.

The sintered samples were further analysed with respect to their color (L*a*b* values), translucency (T) and fluorescence effect. The results are given in Tables 3a, 3b and 3c. The differences d L*, d a* and d b* were calculated with respect to the Sinter Protocol-Fast 1. The values shown for each sintering process were averaged over at least 11 samples.

Chromium

TABLE 3a

| | color values (L*, a* and b*), translucency (T), and visible fluorescence effect. | | | | | | | |
|---|---|---|---|---|---|---|---|---|
| Sample | L* | a* | b* | d L*/% | d a*/% | d b*/% | T/% | Fluorescence |
| SP-F1 | 70.04 | 7.18 | 19.36 | 0.00 | 0.00 | 0.00 | 18.72 | yes |
| SP-F2 | 70.48 | 6.95 | 19.87 | 0.63 | −3.14 | 2.61 | 19.45 | yes |
| SP-R1 | 70.35 | 7.11 | 22.12 | 0.44 | −0.89 | 14.27 | 20.31 | yes |
| SP-R2 | 70.44 | 7.20 | 22.77 | 0.57 | 0.33 | 17.61 | 18.77 | yes |

Manganese

TABLE 3b

| | color values (L*, a* and b*), translucency (T), and visible fluorescence effect. | | | | | | | |
|---|---|---|---|---|---|---|---|---|
| Sample | L* | a* | b* | d L*/% | d a*/% | d b*/% | T/% | Fluorescence |
| SP-F1 | 68.69 | 5.87 | 9.05 | 0.00 | 0.00 | 0.00 | 16.72 | yes |
| SP-F2 | 67.62 | 5.63 | 9.83 | −1.56 | −4.06 | 8.57 | 16.46 | yes |
| SP-R1 | 66.63 | 5.39 | 11.81 | −3.00 | −8.14 | 30.39 | 16.19 | yes |
| SP-R2 | 66.67 | 5.86 | 11.43 | −2.94 | −0.04 | 26.20 | 14.72 | yes |

Cobalt

TABLE 3c

| | color values (L*, a* and b*), translucency (T), and visible fluorescence effect. | | | | | | | |
|---|---|---|---|---|---|---|---|---|
| Sample | L* | a* | b* | d L*/% | d a*/% | d b*/% | T/% | Fluorescence |
| SP-F1 | 75.01 | 6.52 | 17.23 | 0.00 | 0.00 | 0.00 | 19.19 | yes |
| SP-F2 | 74.77 | 6.22 | 17.54 | −0.31 | −4.70 | 1.75 | 20.34 | yes |
| SP-R1 | 73.95 | 6.02 | 20.10 | −1.41 | −7.66 | 16.62 | 21.56 | yes |
| SP-R2 | 72.95 | 6.03 | 20.95 | −2.75 | −7.54 | 21.59 | 21.20 | yes |

All samples showed tooth-like fluorescence under UV light. Neither Cr, Mn or Co seemed to prevent fluorescence at the examined amount.

The L* and a* values of the Cr samples were stable over different sintering conditions. The b* value showed more difference between SP-F1/SP-F2 and SP-R1/SP-R2. This change might be caused by the presence of Tb (the yellow shading component), that yields a higher b* value with increased sintering time (especially between 40 and 70 min sintering time). This behavior was inherent to all Tb containing samples.

The Mn samples showed a greater variation of all values (L*, a* and b*) over the different sintering conditions compared to the Cr samples. Especially the relative variation of the b* value was stronger. In addition, the absolute b* values were about only half as high (when Mn was used), i.e. Mn decreased the yield of b* value per applied amount of Tb. This is undesired, because a higher amount of valuable and expensive Tb component would be needed to achieve the same level of yellow color.

The Co samples, like the Mn samples, showed a greater variation of all values (L*, a* and b*) over the different sintering conditions compared to the Cr samples. However, this variation was less severe than in the case of the Mn samples. But the absolute L* values of the Co samples were higher than those of the Cr or the Mn samples. The ability of Co to produce a grey shade seems to be inferior to Cr and Mn. Therefore, a higher amount of Co would be necessary to produce the same amount of grey shade. This again might lead to higher variations of L*, a* and b* value under different sintering conditions.

In conclusion, the use of Tb lead to a variation of the b* value under different sintering conditions. The presence of Cr, Mn or Co can influence, how pronounced this variation is. The use of Cr has been proven to not only to minimize the variation of the b* value, but also of the L* and a* value. There may be yellow shading components that show even less variation of the b* value than Tb, but the use of Tb is still preferred because it yields a yellow color and at the same time does not prevent tooth-like fluorescence.

Therefore, the combination of Bi, Er, Tb and Cr is beneficial for producing a fluorescing dental zirconia restoration with a stable shade or color.

The invention claimed is:

1. A process of producing a dental mill blank comprising a porous zirconia material,
the porous zirconia material comprising Zr oxide, and Y oxide calculated as $Y_2O_3$: 13 to 15 wt. %,
the porous zirconia material not comprising
Fe oxide calculated as $Fe_2O_3$ of more than 0.01 wt. %,
Mn oxide calculated as $MnO_2$ of more than 0.005 wt. %, or
Co oxide calculated as $Co_2O_3$ of more than 0.005 wt. %,
the wt. % is calculated with respect to the weight of the porous zirconia material,
wherein the porous zirconia material is further characterized by a biaxial flexural strength of greater than 40 MPa to 80 MPa,
the process comprising the steps of
providing a first zirconia powder comprising Tb oxide,
providing a second zirconia powder comprising Er oxide in an amount of 0.5 to 12.0 wt. %,
mixing and layering a plurality of zirconia powders including the first zirconia powder and the second zirconia powder,
compacting the layered and mixed zirconia powders to provide a compacted zirconia mixture, and
sintering the compacted zirconia mixture to produce the dental mill blank.

2. The process of claim 1, wherein the porous zirconia material does not comprise at least one of the following components:
oxide(s) selected from Dy, Sm, Nd, Eu, Cu, V, Mo, Ni, each in an amount above 0.01 wt. %,
glass in an amount above 1 wt. %,
glass ceramic in an amount above 1 wt. %,
lithium (di) silicate ceramic in an amount above 1 wt. %, or
combinations thereof,
the wt. % is calculated with respect to the weight of the porous zirconia material.

3. The process of claim 1, wherein the porous zirconia material is characterized by the following features alone or in combination:

(a) average grain size: less than 100 nm;

(b) average connected pore diameter: 10 to 100 nm;

(c) BET surface: 2 to 20 $m^2$/g; or (d) Vickers hardness: 25 (HV 0.5) to 150 (HV 1).

4. The process of claim 1, wherein the porous zirconia material further comprises the respective oxides in the following amounts:

Zr oxide calculated as $ZrO_2$: 80 to 96 wt. %,

Y oxide calculated as $Y_2O_3$: 14 to 15 wt. %,

Al oxide calculated as $Al_2O_3$: 0 to 0.15 wt. %,

Bi oxide calculated as $Bi_2O_3$: 0.01 to 0.2 wt. %,

Tb oxide calculated as $Tb_4O_7$: 0.01 to 0.8 wt. %,

Er oxide calculated as $Er_2O_3$: 0.01 to 3.0 wt. %, and

Cr oxide calculated as $Cr_2O_3$: 0.0001 to 0.1 wt. %, the wt. % is calculated with respect to the weight of the porous zirconia material.

5. The process of claim 1, wherein the dental mill blank is characterized by the following features alone or in combination:

shape: cubic, cuboid, cylindric, disc-shaped;

size:

for cubic or cuboid shaped blanks: more than 19 mm in 2 dimensions, more than 12 mm in a particular dimension; or for cylindric or disc shaped blanks: more than 19 mm in diameter, more than 12 mm in height; or comprising means for attaching the dental mill blank to a machining device.

6. The process of claim 1, wherein the dental mill blank is characterized as follows:

having a shape of a cube, rectangular prism, cylinder or disc, and comprising means for attaching the dental mill blank to a machining device, the porous zirconia material being characterized as follows:

BET surface: 2 to 20 $m^2$/g;

biaxial flexural strength: 8 to 80 MPa;

x, y dimension: at least 19 mm;

z dimension: at least 12 mm; or

Density: 30 to 95% of theoretical density;

the porous zirconia material comprising:

Zr oxide calculated as $ZrO_2$: 80 to 96 wt. %,

Al oxide calculated as $Al_2O_3$: 0 to 0.15 wt. %,

Y oxide calculated as $Y_2O_3$: 14 to 15 wt. %,

Bi oxide calculated as $Bi_2O_3$: 0.01 to 0.2 wt. %,

Tb oxide calculated as $Tb_4O_7$: 0.01 to 0.8 wt. %,

Er oxide calculated as $Er_2O_3$: 0.2 to 1.2 wt. %, and

Cr oxide calculated as $Cr_2O_3$: 0.0005 to 0.006 wt. %, the porous zirconia material not comprising:

Fe oxide calculated as $Fe_2O_3$ in an amount of more than 0.01 wt. %,

Mn oxide calculated as $MnO_2$ in an amount of more than 0.005 wt. %,

Co oxide calculated as $Co_2O_3$ in an amount of more than 0.005 wt. %, or a glass, glass ceramic or lithium disilicate material above 1 wt. %, the wt. % is calculated with respect to the weight of the porous zirconia material.

7. A process of producing a dental restoration, the process comprising the steps of:

providing a dental mill blank obtained by the process of claim 1, machining the dental restoration out of the porous zirconia material of the dental mill blank, and sintering the dental restoration.

8. The process of producing a dental restoration according to claim 7, the sintering being done by applying either of the following heat-treatment steps:

sintering step comprising a heating rate of 1 to 60° C./min; and sintering step comprising a heating rate of 1.5 to 7° C./sec.

9. The process of producing a dental restoration according to claim 7, the sintering of the dental restoration being done by applying the following conditions:

heating rate in a range of 2 to 7° C./sec;

sintering temperature of at least 1,500° C.; and duration of less than 60 min.

10. The process of claim 1, wherein none of the zirconia powders or the dental mill blank comprise:

Fe oxide calculated as $Fe_2O_3$ in an amount of more than 0.01 wt. %,

Mn oxide calculated as $MnO_2$ in an amount of more than 0.005 wt. %, or

Co oxide calculated as $Co_2O_3$ in an amount of more than 0.005 wt. %.

11. The process of claim 1, wherein the porous zirconia material comprises an average grain size of less than 100 nm.

* * * * *